(12) United States Patent
Lurvink et al.

(10) Patent No.: US 8,481,493 B2
(45) Date of Patent: *Jul. 9, 2013

(54) NON-POROUS FILM FOR CULTURING CELLS

(75) Inventors: Raymond Lurvink, Udenhout (NL); Peter Franciscus Theresius Maria van Asten, Hilvarenbeek (NL); Jan Bastiaan Bouwstra, Bilthoven (NL); Sebastianus Gerardus Johannes Maria Kluijtmans, Zeist (NL)

(73) Assignee: Fujifilm Manufacturing Europe B.V., Tilburg (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/531,414

(22) Filed: Jun. 22, 2012

(65) Prior Publication Data

US 2012/0264695 A1    Oct. 18, 2012

Related U.S. Application Data

(63) Continuation of application No. 11/910,824, filed as application No. PCT/NL2006/050075 on Apr. 6, 2006, now Pat. No. 8,227,415.

(60) Provisional application No. 60/751,632, filed on Dec. 20, 2005.

(51) Int. Cl.
*A61K 38/39* (2006.01)
*A61K 47/48* (2006.01)

(52) U.S. Cl.
USPC ........................................................ 514/17.2

(58) Field of Classification Search
None
See application file for complete search history.

(56) References Cited

U.S. PATENT DOCUMENTS

| 4,016,877 A | 4/1977 | Cruz et al. |
| 4,294,241 A | 10/1981 | Miyata |
| 4,963,146 A | 10/1990 | Li |
| 5,206,028 A | 4/1993 | Li |
| 6,039,760 A * | 3/2000 | Eisenberg ................. 623/15.12 |
| 6,500,464 B2 | 12/2002 | Ceres et al. |
| 7,670,839 B2 | 3/2010 | Bouwstra et al. |
| 8,227,415 B2 * | 7/2012 | Lurvink et al. ............. 514/17.2 |
| 2004/0191190 A1 | 9/2004 | Pauly et al. |
| 2007/0004034 A1 * | 1/2007 | Bouwstra et al. ......... 435/289.1 |

FOREIGN PATENT DOCUMENTS

| EP | 0 243 132 B1 | 3/1991 |
| EP | 0 177 573 B1 | 1/1992 |
| EP | 0 411 124 B1 | 10/1993 |
| EP | 0 403 650 B1 | 5/1994 |
| EP | 0 686 402 A1 | 12/1995 |
| EP | 1 398 324 A1 | 3/2004 |
| EP | 0 702 081 B1 | 3/2006 |
| WO | WO-80/01350 A1 | 7/1980 |
| WO | WO-91/16010 A1 | 10/1991 |
| WO | WO-92/10217 A1 | 6/1992 |
| WO | WO-98/16165 A1 | 4/1998 |
| WO | WO-00/09018 A1 | 2/2000 |
| WO | WO-03/101501 A1 | 12/2003 |
| WO | WO-2004/078120 A2 | 9/2004 |
| WO | WO-2004/085473 A2 | 10/2004 |

OTHER PUBLICATIONS

Harada, et al. Collagen-Based New Biomedicial Films: Synthesis, Property and Cell Adhesion. Journal of Applied Polymer Science. vol. 81, pp. 2433-2438, 2001.
International Search Report for PCT/NL2005/000261, dated Jun. 7, 2006, 3 pages.
International Search Report on Application No. PCT/NL2006/050075 dated May 25, 2007.
Ramshaw, et al. Gly-X-Y Tripeptide Frequencies in Collagen: A Context for Host-Guest Triple-Helical Peptides. Journal of Structural Biology, 1998. vol. 122, pp. 86-91.

* cited by examiner

*Primary Examiner* — Marcela M Cordero Garcia
(74) *Attorney, Agent, or Firm* — Gilberto M. Villlacorta; Sunit Talapatra; Foley & Lardner LLP (57) ABSTRACT

The invention relates to collagenous polypeptide films on which cells are cultivated. In particular the invention relates to such films that are used to treat wounds such as severe burns or physical or chemical injury. The invention also related to methods for producing such films.

13 Claims, 2 Drawing Sheets

NON-POROUS FILM FOR CULTURING CELLS

CROSS-REFERENCE TO RELATED APPLICATION(S)

This application is a Continuation of U.S. patent application Ser. No. 12/848,877, which is the National Phase of International Patent Application No. PCT/NL2006/050075, filed Apr. 6, 2006, which claims the benefit of U.S. Provisional Application No. 60/751,632, filed Dec. 20, 2005. The contents of these applications are herein incorporated by reference in their entirety.

FIELD OF THE INVENTION

The invention relates to gelatin comprising films on which cells can be or are cultivated. In particular the invention relates to such films that are used to treat wounds, such as severe burns or physical or chemical injury of the skin or wounds caused by diseases. The invention also related to methods for producing such films and the use of such films. In a further aspect of the invention human artificial skin grown on such films are provided, and methods of making these.

BACKGROUND

Films on which cells are cultured are used in the treatment of skin wounds such as for example wounds caused by severe burns or mechanical or chemical injuries or in diseases where extensive loss of skin occurred. In cases of acute extensive skin loss treatment generally involves two phases. In the first phase the requirements for a film material are directed towards short term requirements such as controlling moisture flow through the wound and shielding from infectious agents. In the second stage long term effects are considered such as non-antigenicity, and skin regeneration.

Development of such materials is in the direction of multilayer materials of increasing complexity as described in, for example, EP 0 686 402, WO 03/101501. Many patent applications disclose the use of porous collagen or gelatin matrices or sponges that require the formation of collagen fibrils and forming of a porous network, for example by freeze drying, before crosslinking the porous matrices as in for example EP 0 177 573, EP 0 403 650, EP 0 403 650, EP 0 411 124, EP 0 702 081, U.S. Pat. No. 4,016,877 and U.S. Pat. No. 4,294,241.

In applications for wound treatment fibroblast and keratinocyte layers are cultured on a collagen or gelatin matrix. In such cultures the fibroblast cells and/or keratinocyte cells are usually actually embedded in the matrix material, due to the porous nature of the collagen or gelatin matrix. EP 0 243 132 describes culturing of fibroblasts on an insoluble collagen film and the subsequent culturing of keratinocytes on top of the fibroblast layer, but has as a drawback that the fibroblast and keratinocyte layers are in contact.

WO 80/01350 discloses production of a living tissue by culturing keratinocytes on a collagen layer in which fibroblasts are imbedded, but this also means that the fibroblast layer and the keratinocyte layers are in contact.

WO 91/16010 describes a complex material based on a non-porous collagen gel that is stabilized by iodine and which is laminated on top of a porous collagen sponge containing fibroblasts. Keratinocytes are cultured on top of the stabilized collagen gel. The porous collagen sponge is crosslinked to prevent too fast biodegradation.

Use of recombinant collagen or gelatin is disclosed in e.g. WO 00/09018 but describes the formation of crosslinked sponges of collagen fibrils. WO 04/78120 also discloses porous structures from recombinant collagen.

Films are also used to test for example allergic reactions to topical applications comprising medicines, pharmaceuticals or cosmetics.

In spite of the above described materials there remains a need for alternative films for culturing cells that are suitable for treatment of wounds involving the loss of skin.

SUMMARY OF THE INVENTION

It is an object of the invention to provide a film suitable for making a human artificial skin equivalent and a method for making such a skin equivalent. It is especially an object to provide a film which enables rapid growth of autologous cells on it surfaces and which enhances cell attachment (adhesion) to the film and cell-to-cell binding of the autologous cells. More specifically it is an object to provide a full equivalent of human skin. It is further an object of the invention to provide a method to produce such a film cheap and efficiently with high speed.

Thus it is an object of this invention to provide a non-antigenic film suitable for culturing human and/or mammalian cells of which the biodegradability can be regulated, and particularly it is an objective to provide such a film that is permeable to molecules, including polypeptides and proteins, of up to 25 kilo Dalton.

It is also an objective of the invention to provide a film which is suitable as a test substrate for medicines, pharmaceuticals or cosmetics. In particular the effect of compounds contacted with living or viable cells present on the film can be tested.

Surprisingly it was found that all these objectives were met by a non-porous film comprising on at least one side thereof a layer comprising living or viable cells and wherein the non-porous film comprises a collagenous polypeptide comprising at least one GXY domain having a length of at least 5 consecutive GXY triplets, wherein X and Y each represent any amino acid and wherein at least 20% of the amino acids of said collagenous polypeptide are present in the form of consecutive GXY triplets, characterized in that the film thickness when placed in demineralized water of 37 degrees Celsius for 24 hours is at most 10 times its initial thickness.

The non-porous film preferably comprises a collagenous polypeptide comprising at least one GXY domain having a length of at least 5 consecutive GXY triplets, wherein X and Y each represent any amino acid and wherein at least 20% of the amino acids of said collagenous polypeptide are present in the form of consecutive GXY triplets, characterized in that said film is crosslinked by adding between 0.02 millimol and 5.0 millimol of a crosslinking compound per gram collagenous polypeptide.

DESCRIPTION OF THE INVENTION

When extensive skin loss occurs, wounds are generally treated in two phases. There remains a need for films that can specifically be matched to the requirements of each treatment phase or more specifically, to the desired biodegradation speed while being sufficiently permeable to compounds that are involved in culturing cells on the film, specifically for compounds that promote growth of cells on both sides of the film.

The present inventors found that such films can be made which are matched to the requirements of each treatment phase by careful choice of the swelling behavior and permeability. Swelling behavior is the increase of the initial thickness of a non-porous collagenous polypeptide film when placed in a liquid. In the art it is taught that a pore size of at least 1 micron is necessary to provide enough permeability for compounds involved in wound healing such as nutrients and growth factors, especially when fibroblasts and keratinocytes are present within a matrix or in different matrices, see for example EP-0 702 081 and also the reference in column 4, lines 44-49 therein. The present inventors found, however, that films that are non-porous, or have an average pore-size of less than 1 micron, are capable of taking up water and are permeable for compounds involved in wound healing. Although it was recognized in prior art as early as 1976, or even earlier, that crosslinking is necessary to prevent too fast biodegradation, it was not recognized until now that the degree of crosslinking can be advantageously used to adjust swellability and thus biodegradability and permeability. Thus the use of films of this invention for the preparation of a composition for treating wounds is an aspect of this invention. The films of this invention can be used to match any particular treatment, especially first phase or second phase treatment, by providing a non-porous film comprising on at least one side thereof a layer comprising living or viable cells and wherein the non-porous film thickness increases up to 10 times its initial thickness when placed in demineralized water at 37 degrees Celsius. Depending on the desired permeability or biodegradability the film swells at most 8 times, or at most 6 times or at most 4 times its original thickness in water.

Preferably the film swells at least 2 times its original thickness in water. In particular, a method was developed to produce non-porous films having a desired degree of cross-linking and therefore also a desired biodegradation speed and permeability in vivo (after contact with skin wounds e.g. during treatment phase one or two). In one embodiment of the invention films with a desired, predetermined degree of cross linking are non-porous films (suitable for cultivating living or cells on at least one side thereof) comprising a collagenous polypeptide that comprises at least one GXY domain having a length of at least 5 consecutive GXY triplets, wherein X and Y each represent any amino acid and wherein at least 20% of the amino acids of said collagenous polypeptide are present in the form of consecutive GXY triplets. In one embodiment the films according to the invention are crosslinked by adding one or more crosslinking compounds in an amount of between about 0.02 and 5.0 millimol per gram collagenous polypeptide, preferably between 0.1 to 1.0 millimol/g. In another embodiment no cross-linking compound is present, but the (equivalent) degree of cross-linking is achieved by radiation. In yet another embodiment cross-linking is achieved by a combination of radiation and addition of one or more cross-linking compounds.

A further advantage of the method and films according to the invention is, that the step of forming fibrils, which is necessary when making porous structures is now obsolete. Further, also the step of freeze drying which is involved in obtaining a porous material is now obsolete, (although both steps may still optionally be carried out) thereby reducing the time and energy that is involved in producing artificial skin and making it possible to produce the non-porous film of this invention efficiently and with high speed.

The term "non-porous" means that essentially no micropores are formed as in for example EP 0 177 573, EP 0 403 650, EP 0 403 650, EP 0 411 124, EP 0 702 081, U.S. Pat. No. 4,016,877 or U.S. Pat. No. 4,294,241. The term 'porous' or 'macroporous' can be ambiguous, and one may define a crosslinked collagen or gelatin layer as being 'porous' on a nano-scale. In the broadest sense, non-porous means in this case that the average pore-size is less than 1 micron, as determined by scanning electron microscopy (SEM) described in for example by Dagalakis et. al. (Design of an artificial skin Part III Control of pore structure—Journal of Biomedical Materials Research, Vol. 14, 519 (1980)).

The non-porous film is however permeable for molecules, including polypeptides or proteins, of up to 5 kilo Dalton, preferably up to 10 kilo Dalton and more preferably up to 25 kilo Dalton. In comparison to a globular protein, permeability of a linear protein such as for example a collagen may be higher, up to between 30 and 40 kilo Dalton.

In one embodiment crosslinking of the collagenous polypeptide is achieved by addition of one or more crosslinking agents. These comprise agents that start crosslinking spontaneously upon addition to collagenous polypeptide solution, or after adjusting for example, pH, or by photo initiation or other activation mechanisms. In this particular embodiment a number of millimol crosslinks per gram collagenous polypeptide is defined as being equal to the amount of crosslinking agent that has reacted with the collagenous polypeptide.

In another embodiment crosslinking of the collagenous polypeptide is achieved by exposure to radiation such as UV-radiation or electron beam. In this particular embodiment of the invention a number of millimol crosslinks is defined as the amount of crosslinking agent that would need to be added to obtain the same number of crosslinks as are obtained by exposure to radiation. In other words, the exposure to radiation results in an equivalent degree of cross-linking as the addition of between about 0.02 millimol to about 5.0 millimol of crosslinking compound per gram collagenous polymer does. The amount of crosslinking agent to be added to obtain a certain number of crosslinks can be calculated or determined experimentally. In case of exposure to radiation the required exposure time and intensity has to be determined experimentally, but this is within the capability of a skilled person without undue burden. The degree of crosslinking can be determined in several ways. In one method, the degree of swelling of the crosslinked collagenous polypeptide is measured by soaking the film in demineralized water and measuring the increase in thickness (swelling) or the increase in weight resulting from water uptake. A series of radiation exposures is then compared to a series in which varying amounts of crosslinking agent is added. Comparing the results of a swelling test provides a correlation between the two methods of crosslinking. A method for measuring swelling of collagenous films is described for example by Flynn and Levine (Photogr. Sci. Eng., 8, 275 (1964).

Suitable crosslinking agents are preferably those that do not elicit toxic or antigenic effects when released during biodegradation. Suitable crosslinking agents are, for example, one or more of glutaraldehyde, water-soluble carbodiimides, bisepoxy compounds, formalin, 1-ethyl-3-(3-dimethylaminopropyl) carbodiimide, N-hydroxy-succinimide, glycidyl ethers such as alkylene glycol diglycidyl ethers or polyglycerol polyglycidyl ether, diisocyanates such as hexamethylene diisocyanate, diphenylfosforylazide, D-ribose. Crosslinking techniques are also described by Weadock et. al. in Evaluation of collagen crosslinking techniques (Biomater. Med. Devices Artif. Organs, 1983-1984, 11(4): 293-318). In a preferred embodiment water-soluble 1-ethyl-3-(3-dimethylaminopropyl) carbodiimide is used.

In one embodiment the film is particularly suitable for the first phase treatment and is crosslinked by adding between 0.02 and 1.0 millimol crosslinking compound(s) per gram collagenous polypeptide (or radiation induced crosslinking which is equivalent hereto). Thus, the cross-linking compound(s) may be present in an amount of about 0.02, 0.05, 0.1, 0.25, 0.5, 0.6, 0.7, 0.8, 0.9 or 1.0 millimol/gram polypeptide.

In another embodiment the film is particularly suitable for second phase treatment and is crosslinked by adding between 0.5 and 5.0 millimol crosslinking compound(s) per gram collagenous polypeptide (or radiation induced crosslinking which is equivalent hereto), preferably about 1.0 to 2.5 millimol/g. Thus, the cross-linking compound(s) may be present in an amount of about 0.5, 0.6, 0.7, 0.8, 0.9, 1.0, 2.0, 3.0, 4.0 and 5.0 millimol/gram polypeptide.

In yet another embodiment the film can be used as an intermediate between first and second phase treatment and is crosslinked by adding between 0.25 and 2.5 millimol crosslinking compound(s) per gram collagenous polypeptide (or radiation induced crosslinking which is equivalent hereto).

Another way to express the amount of crosslinking agent is the molar ratio with lysine residues in the polypeptide. Especially in case of recombinantly produced collagenous polypeptides the number of lysine residues can be increased as desired. Many crosslinking agents bind to lysine residues and/or N-terminal amines. Natural gelatin contains between 25 and 27 lysines per 1000 amino acids. In recombinant collagens or collagenous polypeptides this can be reduced to for example equal to or less than about 20, 15, 10 or 5 lysines per 1000 amino acids or increased to for example equal to or more than about 30, 40 or 50 lysines per 1000 amino acids.

For example, a recombinant collagen-like polypeptide monomer is described in EP1 398 324 that contains 8 lysines in a sequence of 204 amino acids, or 39 lysines per 1000 amino acids.

Preferably the non-porous films according to the invention comprise between 0.01 and 12.5 millimol crosslinking compound(s) per millimol lysine in the collagenous polypeptide, or between 0.1 and 10 millimol per millimol lysine or between 1 and 5 millimol per millimol lysine, depending on the amount of lysines present in the collagenous polypeptide.

Suitable collagenous polypeptides to make the films according to the invention are collagens or gelatins from natural, synthetic or recombinant sources or mixtures thereof. Although strictly speaking there is a difference between collagen and gelatin, these differences are in principle not essential to the invention, although specific requirements may make the selection of collagen or gelatin for a certain application obvious. In this respect "collagen" may also be read as "gelatin" and "collagenous polypeptide" may also be read as "gelatinous polypeptide". A collagenous or gelatinous polypeptide is thus defined as being a polypeptide in which at least one GXY domain is present of at least a length of 5 consecutive GXY triplets and at least 20% of the amino acids of the collagenous polypeptide are present in the form of consecutive GXY triplets, wherein a GXY triplet consists of G representing glycine and X and Y representing any amino acid. Suitably at least 5% of X and/or Y can represent proline and in particular at least 5%, more in particular between 10 and 33% of the amino acids of the GXY part of the collagenous polypeptide is proline. Collagenous polypeptides which can be obtained from natural gelatin can be for example alkaline processed gelatin, acid processed gelatin, hydrolyzed gelatin or peptized gelatin resulting from enzymatic treatment. Natural sources can be the skin or bones of mammals such as cattle or pigs but also of cold-blooded animals such as fish.

The collagenous polypeptide preferably has an average molecular weight of less than 150 kilo Dalton, preferably of less than 100 kilo Dalton. Ranges of between 50 an 100 kilo Dalton are suitable or hydrolyzed collagenous polypeptides of less than 50 kilo Dalton or between 5 and 40 kilo Dalton may be used. Preferably the collagenous polypeptides have an average molecular weight of at least 5 kilo Dalton, preferably at least 10 kilo Dalton and more preferably of at least 30 kilo Dalton. A smaller average molecular weight means that more crosslinking compound(s) should be added to obtain a certain permeability than with larger polypeptides. However, lower molecular weights may be preferred for example in production of the non-porous film where lower molecular weight has a lower viscosity which makes higher concentrations of collagenous polypeptides possible.

The method of making recombinant collagenous polypeptides has been described in detail in U.S. Pat. No. 6,150,081 and US 2003/229205 by the same applicant, the content of which is herein incorporated by reference. The methodology is described in the publication 'High yield secretion of recombinant gelatins by *Pichia pastoris*', M. W. T. Werten et al., Yeast 15, 1087-1096 (1999).

Recombinantly produced collagenous polypeptides are preferred because the detrimental effects involved in using gelatin or collagen from animal sources, such as for example BSE, are avoided. Also, better control of parameters such as size distribution, amino acid sequence or the occurrence of specific amino acids is possible. Preferably such recombinant collagenous polypeptides have even lower antigenicity than natural gelatins.

In one embodiment the recombinant collagenous polypeptide does not form stable triple helices, specifically not at temperature of more than 5 degrees Celsius, or at temperatures higher than 25 degrees Celsius. Such collagenous polypeptides have preferably an amount of prolines present in GXY triplets that is comparable to collagen originating from mammals or collagens originating from cold-blooded animals such as fish. To prevent stable triple helix formation less than 2 number percent, preferably less than 1 number percent, of the amino acids present in the collagenous polypeptide are hydroxylated. Occurrence of hydroxyprolines can be reduced to be practically zero by expression in micro organisms that do not co-express a prolylhydroxylase or fulfill that function in another way. Practically zero means that the presence of hydroxyprolines in the growth medium of for example yeasts may result in incorporation of some of these amino acids into the collagenous polypeptide. Recombinant collagen-like polypeptides that are not hydroxylated and have the advantage of avoiding the occurrence of anaphylactic shock are described in EP 1 238 675.

In a preferred embodiment the non-porous film comprises collagenous polypeptides with excellent cell attachment properties, and which do not display any health related risks, by production of RGD-enriched collagenous polypeptides in which the percentage of RGD motifs related to the total number of amino acids is at least 0.4. If the RGD-enriched collagenous polypeptide comprises 350 amino acids or more, each stretch of 350 amino acids contains at least one RGD motif. Preferably the percentage of RGD motifs is at least 0.6, more preferably at least 0.8, more preferably at least 1.0, more preferably at least 1.2 and most preferably at least 1.5.

A percentage RGD motifs of 0.4 corresponds with at least 1 RGD sequence per 250 amino acids. The number of RGD motifs is an integer, thus to meet the feature of 0.4%, a collagenous polypeptide consisting of 251 amino acids should comprise at least 2 RGD sequences. Preferably the RGD-enriched recombinant collagenous polypeptide comprises at least 2 RGD sequence per 250 amino acids, more preferably at least 3 RGD sequences per 250 amino acids, most preferably at least 4 RGD sequences per 250 amino acids. In a further embodiment an RGD-enriched collagenous polypeptide comprises at least 4 RGD motifs, preferably 6, more preferably 8, even more preferably 12 up to and including 16 RGD motifs.

The term 'RGD-enriched collagenous polypeptide' in the context of this invention means that the collagenous polypeptides have a certain level of RGD motifs, calculated as a percentage of the total number of amino acids per molecule and a more even distribution of RGD sequences in the amino acid chain than a natural gelatin. In humans up to date 26 distinct collagen types have been found on the basis of protein and or DNA sequence information (see K. Gelse et al, Collagens-structure, function and biosynthesis, Advanced Drug Delivery reviews 55 (2003) 1531-1546). Sequences of natural gelatins, both of human and non-human origin, are described in the Swiss-Prot protein database. Here below follows a list of suitable human native sequences, identified by their entry name and primary accession number in the Swiss-Prot database, that may serve as a source of parts of natural sequences comprised in the RGD-enriched collagenous polypeptides comprised in the non-porous films of this invention.

CA11_HUMAN (P02452) Collagen alpha 1(I) chain precursor. {GENE: COL1A1}—*Homo sapiens* (Human)
CA12_HUMAN (P02458) Collagen alpha 1(II) chain precursor [Contains: Chondrocalcin]. {GENE: COL2A1}—*Homo sapiens* (Human)
CA13_HUMAN (P02461) Collagen alpha 1(III) chain precursor. {GENE: COL3A1}—*Homo sapiens* (Human)
CA14_HUMAN (P02462) Collagen alpha 1(IV) chain precursor. {GENE: COL4A1}—*Homo sapiens* (Human)
CA15_HUMAN (P20908) Collagen alpha 1(V) chain precursor. {GENE: COL5A1}—*Homo sapiens* (Human)
CA16_HUMAN (P12109) Collagen alpha 1(VI) chain precursor. {GENE: COL6A1}—*Homo sapiens* (Human)
CA17_HUMAN (Q02388) Collagen alpha 1(VII) chain precursor (Long-chain collagen) (LC collagen). {GENE: COL7A1}—*Homo sapiens* (Human)
CA18_HUMAN (P27658) Collagen alpha 1(VIII) chain precursor (Endothelial collagen). {GENE: COL8A1}—*Homo sapiens* (Human)
CA19_HUMAN (P20849) Collagen alpha 1(IX) chain precursor. {GENE: COL9A1}—*Homo sapiens* (Human)
CA1A_HUMAN (Q03692) Collagen alpha 1(X) chain precursor. {GENE: COL10A1}—*Homo sapiens* (Human)
CA1B_HUMAN (P12107) Collagen alpha 1(XI) chain precursor. {GENE: COL11A1}—*Homo sapiens* (Human)
CA1C_HUMAN (Q99715) Collagen alpha 1(XII) chain precursor. {GENE: COL12A1}—*Homo sapiens* (Human)
CA1E_HUMAN (P39059) Collagen alpha 1(XV) chain precursor. {GENE: COL15A1}—*Homo sapiens* (Human)
CA1F_HUMAN (Q07092) Collagen alpha 1(XVI) chain precursor. {GENE: COL16A1}—*Homo sapiens* (Human)
CA1G_HUMAN (Q9UMD9) Collagen alpha 1(XVII) chain (Bullous pemphigoid antigen 2) (180 kDa bullous pemphigoid antigen 2). {GENE: COL17A1 OR BPAG2 OR BP180}—*Homo sapiens* (Human)
CA1H_HUMAN (P39060) Collagen alpha 1(XVIII) chain precursor [Contains: Endostatin]. {GENE: COL18A1}—*Homo sapiens* (Human)
CA1I_HUMAN (Q14993) Collagen alpha 1(XIX) chain precursor (Collagen alpha 1(Y) chain). {GENE: COL19A1}—*Homo sapiens* (Human)
CA21_HUMAN (P08123) Collagen alpha 2(I) chain precursor. {GENE: COL1A2}—*Homo sapiens* (Human)
CA24_HUMAN (P08572) Collagen alpha 2(IV) chain precursor. {GENE: COL4A2}-*Homo sapiens* (Human)
CA25_HUMAN (P05997) Collagen alpha 2(V) chain precursor. {GENE: COL5A2}—*Homo sapiens* (Human)
CA26_HUMAN (P12110) Collagen alpha 2(VI) chain precursor. {GENE: COL6A2}—*Homo sapiens* (Human)
CA28_HUMAN (P25067) Collagen alpha 2(VIII) chain precursor (Endothelial collagen). {GENE: COL8A2}—*Homo sapiens* (Human)
CA29_HUMAN (Q14055) Collagen alpha 2(IX) chain precursor. {GENE: COL9A2}—*Homo sapiens* (Human)
CA2B_HUMAN (P13942) Collagen alpha 2(XI) chain precursor. {GENE: COL11A2}—*Homo sapiens* (Human)
CA34_HUMAN (Q01955) Collagen alpha 3(IV) chain precursor (Goodpasture antigen). {GENE: COL4A3}—*Homo sapiens* (Human)
CA35_HUMAN (P25940) Collagen alpha 3(V) chain precursor. {GENE: COL5A3}—*Homo sapiens* (Human)
CA36_HUMAN (P12111) Collagen alpha 3(VI) chain precursor. {GENE: COL6A3}—*Homo sapiens* (Human)
CA39_HUMAN (Q14050) Collagen alpha 3(IX) chain precursor. {GENE: COL9A3}—*Homo sapiens* (Human)
CA44_HUMAN (P53420) Collagen alpha 4(IV) chain precursor. {GENE: COL4A4}—*Homo sapiens* (Human)
CA54_HUMAN (P29400) Collagen alpha 5(IV) chain precursor. {GENE: COL4A5}—*Homo sapiens* (Human)
CA64_HUMAN (Q14031) Collagen alpha 6(IV) chain precursor. {GENE: COL4A6}—*Homo sapiens* (Human)
EMD2_HUMAN (Q96A83) Collagen alpha 1(XXVI) chain precursor (EMI domain containing protein 2) (Emu2 protein) (Emilin and multimerin-domain containing protein 2). {GENE: EMID2 OR COL26A1 OR EMU2}—*Homo sapiens* (Human)

Natural gelatins are known to comprise RGD sequences. It is important however that a collagenous polypeptide molecule does not contain too large parts without RGD motifs. Too large parts without RGD sequence reduce the possibility of cell attachment when such a collagenous polypeptide is used for instance in tissue engineering applications such as artificial skin. Apparently not all RGD sequences in a collagenous polypeptide are under all circumstances available for cell attachment. It was found that cell attachment was remarkably improved in collagenous polypeptides according to the invention compared to gelatins having a stretch of amino acids of more than 350 without an RGD sequence. For collagenous polypeptides of less than 350 amino acids it is sufficient to have a percentage of RGD sequences of at least 0.4. Note that for a collagenous polypeptide of 251-350 amino acids this means that at least 2 RGD motifs are present.

Thus, either fragments enriched in RGD triplets may be identified in natural collagenous proteins, and/or natural collagenous proteins may be modified generate a polypeptide with a suitable number and distribution of RGD triplets. Nucleic acid sequences encoding suitable polypeptides may then be made and expressed in a suitable host cell or organism.

In a preferred embodiment the RGD-enriched collagenous polypeptide is prepared by recombinant DNA technology. Recombinant collagenous polypeptides of this invention are preferably derived from collagenous sequences. Nucleic acid sequences encoding collagens have been generally described in the art. (See, e.g., Fuller and Boedtker (1981) Biochemistry 20: 996-1006; Sandell et al. (1984) J Biol Chem 259: 7826-34; Kohno et al. (1984) J Biol Chem 259: 13668-13673; French et al. (1985) Gene 39: 311-312; Metsaranta et al. (1991) J Biol Chem 266: 16862-16869; Metsaranta et al. (1991) Biochim Biophys Acta 1089: 241-243; Wood et al. (1987) Gene 61: 225-230; Glumoff et al. (1994) Biochim Biophys Acta 1217: 41-48; Shirai et al. (1998) Matrix Biology 17: 85-88; Tromp et al. (1988) Biochem J 253: 919-912; Kuivaniemi et al. (1988) Biochem J 252: 633640; and Ala-Kokko et al. (1989) Biochem J 260: 509-516.).

For pharmaceutical and medical uses, recombinant collagenous polypeptides with amino acid sequences closely related to or identical to amino acid sequences of natural human collagens are preferred. Amino acid sequences closely related to human collagens (also referred to as proteins which are "essentially similar" to human collagens) are those sequences which comprise at least about 50, 60, 70, 75, 80, 90, 95, 98, 99% or more amino acid sequence identity over the full length to human collagen proteins, such as for example the proteins listed above. Sequence identity is determined using pairwise alignment, whereby two peptide sequences are optimally aligned using programs such as GAP or 'needle' (the equivalent of GAP provided in EmbossWIN v2.10.0) using default parameters. GAP and "needle" uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). Also included are herein fragments of human collagen proteins and of essentially similar proteins, such as fragments of at least 30, 50, 100, 150, 200, 250, 300, 350, 400, 500, 600, 800, 900, 1000 or more consecutive amino acids. As described below, such fragments may also be used to make repeats thereof, such that the fragment is repeated 2, 3, 4, 5, 10, 15, 20, 30, 50, 70, 80, 90 100 times or more. Optionally spacers may be present between the repeats.

More preferably the amino acid sequence of the collagenous polypeptide is designed by a repetitive use of a selected amino acid sequence of a human collagen. A part of a natural collagen sequence comprising an RGD motif is selected. The percentage of RGD motifs in such a selected sequence depends on the chosen length of the selected sequence, selection of a shorter sequence results in a higher RGD percentage. Repetitive use of a selected amino acid sequence results in a gelatin with a higher molecular weight, which is non-antigenic and with an increased number of RGD motifs (compared to natural gelatins or collagens).

Thus in a preferred embodiment the RGD-enriched collagenous polypeptide comprises a part of a native human collagen sequence. Preferably the RGD-enriched collagenous polypeptide consists for at least 80% of one or more parts of one or more native human collagen sequences. Preferably each of such parts of human collagen sequences has a length of at least 30 amino acids, more preferably at least 45 amino acids, most preferably at least 60 amino acids, up to e.g. 240, preferably up to 150, most preferably up to 120 amino acids, each part preferably containing one or more RGD sequences. Preferably the RGD-enriched collagenous polypeptide consists of one or more parts of one or more native human collagen sequences.

An example of a suitable source of a collagenous polypeptide for preparing the films according to this invention is human COL1A1-1. A part of 250 amino acids comprising an RGD sequence is given in WO 04/85473.

RGD sequences in collagenous polypeptides can adhere to specific receptors on the cell wall called integrins. These integrins differ in their specificity in recognizing cell binding amino acid sequences. Although both natural gelatin and, for example, fibronectin may contain RGD sequences, gelatin can bind cells that will not bind to fibronectin and vice versa. Therefore fibronectin comprising RGD sequences cannot always replace gelatin for cell adhesion purposes.

The RGD-enriched collagenous polypeptides can be produced by recombinant methods as disclosed in EP-A-0926543, EP-A-1014176 or WO 01/34646. For the production and purification of collagenous polypeptides that are suited for preparing films of this invention reference is made to the examples in EP-A-0926543 and EP-A-1014176. The preferred method for producing an RGD-enriched collagenous polypeptides is by starting with a natural nucleic acid sequence encoding a part of the collagen protein that includes an RGD amino acid sequence. By repeating this sequence an RGD-enriched collagenous polypeptide is obtained.

If X-RGD-Y is a part of the natural collagen amino acid sequence, a (part of a) collagenous polypeptide with three RGD amino acid sequences would have the structure -X-RGD-Y-(GXYG)m-X-RGD-Y-(GXYG)n-X-RGD-Y-, with m and n being integers starting from 0. By varying n the number of RGD sequences on the total amino acids the percentage of RGD motifs can be controlled. A clear advantage of this method is that the amino acid sequence remains most natural and thus has the lowest risk of inducing immunological response in clinical applications.

Starting from a natural nucleic acid sequence encoding (part of) a collagenous polypeptide, also point mutations can be applied so as to yield a sequence encoding an RGD sequence. Based on the known codons a point mutation can be performed so that an RGX sequence after mutation will yield an RGD sequence, alternatively also an YGD sequence can be mutated to yield an RGD sequence. Also it is possible to carry out two mutations so that an YGX sequence will give an RGD sequence. Also it may be possible to insert one or more nucleotides or delete one or more nucleotides giving rise to a desired RGD sequence.

Further it was found that the properties of the gelatin used to make the film, in terms of the degree of glycosylation, optionally in combination with the number of RGD triplets in the gelatin, can influence the speed of cell growth, the cellular attachment to the film and the cell-to-cell adhesion of the autologous cells, whereby the final thickness and quality (cell density and adhesion strength) of the artificial skin layer can be influenced and improved. Low or no glycosylation of the gelatin used and/or high numbers of RGD triplets in the gelatin used to make the film had a positive effect on the speed of cell (e.g. fibroblast and keratinocyte) growth on the surfaces, and on the cellular adhesion properties. Thus, it was found that by controlling the ratio of glycosylation to the number of RGD triplets, films of good quality can be made.

In a further embodiment, the gelatins used to make the film are low in glycosylation and preferably also substantially pure when used for film making. There are various methods for ensuring that glycosylation is low or absent. Glycosylation is a posttranslational modification, whereby carbohydrates are covalently attached to certain amino acids of the protein or polypeptide. Thus both the amino acid sequence and the host cell (and enzymes, especially glycosyltransferases, therein) in which the amino acid sequence is produced determine the glycosylation pattern. There are two types of glycosylation: N-glycosylation begins with linking of GlcNAc (N-actylglucosamine) to the amide group of asparagines (N or Asn) and O-glycosylation commonly links GalNAc (N-acetylgalactosamine) to the hydroxyl group of the amino acid serine (S or Ser) or threonine (T or Thr).

Glycosylation can, therefore, be controlled and especially reduced or prevented, by choosing an appropriate expression host, and/or by modifying or choosing sequences which lack consensus sites recognized by the hosts glycosyltransferases. Obviously, chemical synthesis of proteins or polypeptides results in unglycosylated proteins. Also, glycosylated proteins may be treated after production to remove all or most of the carbohydrates or unglycosylated proteins may be separated from glycosylated proteins using known methods.

In yeasts N-linked glycosylation of asparagine occurs on the consensus sites Asn-X-Thr or Asn-X-Ser, wherein X is an amino acid. Commonly glycosylation in yeast results in N-linked and O-linked oligosaccharides of mannose. Thus, for expression in yeast the nucleic acid sequence may be modified or selected so that consensus sites are reduced or preferably absent. The Asn codon and/or the Thr codon may be modified, e.g. by mutagenesis or de novo synthesis. Preferably Asn and/or Thr is replaced by another amino acid. Also Asp may be replaced by another amino acid. In one embodiment the polypeptide sequence contains no Ser and/or no Asn.

To analyse the degree of post-translational modification or to determine the content of glycosylation mass spectrometry, such as MALDI-TOF-MS (Matrix Assisted Laser Desorption Ionization mass spectrometry) can be carried out as known in the art.

Alternatively the amount of glycosylation can be determined using the titration method described by Michel Dubois et al, "Colorimetric Method for Determination of Sugars and Related Substances", Analytical Chemistry, vol 28, No. 3, March 1956, 350 356. This method can be used to determine simple (mono) sugars, oligosaccharides, polysaccharides, and their derivatives, including the methyl ethers with free or potentially free reducing groups, and thus the method is quantitative.

The content of glycosylation of the colleganous polypeptide used is preferably equal to, or less than about 2 (m/m) %, more preferably less than about 1 (m/m) %, most preferably less than about 0.5 (m/m) %, 0.2 (m/m) % or 0.1 (m/m) %. In a preferred embodiment the glycosylation content (or degree of glycosylation) is zero. The content of glycosylation refers to the total carbohydrate weight per unit weight of the collagenous polypeptides as determined by for example MALDI-TOF-MS (Matrix Assisted Laser Desorption Ionization mass spectrometry) or preferably the titration method by Dubois et al. referred to above. The term 'glycosylation' refers not only to monosaccharides, but also to poysaccharides such as di-, tri- or tetra saccharides.

In another embodiment the number of RGD triplets (defined as the number of RGD triplets per 250 amino acids of collagenous polypeptide) is preferably at least 2, more preferably at least 3, 4, 5, 6, 7, 8 ore more. Such collagenous polypeptides are referred to as "RGD-enriched collagenous polypeptides".

Thus, in one embodiment a method of making a film which has advantageous properties in the manufacture of artificial skin equivalents is provided. In one embodiment a film is made using collegenous polypeptides having low or no glycosylation and/or a high number of RGD triplets. Film made using the above RGD enriched polypeptides and/or polypeptides low in glycosylation (including polypeptides with zero glycosylation) are also provided. Such film are suitably made as described herein.

Thus the collagenous polypeptides can be produced by expression of nucleic acid sequence encoding such polypeptide by a suitable micro-organism. The process can suitably be carried out with a fungal cell or a yeast cell. Suitably the host cell is a high expression host cells like *Hansenula, Trichoderma, Aspergillus, Penicillium, Saccharomyces, Kluyveromyces, Neurospora* or *Pichia*. Fungal and yeast cells are preferred to bacteria as they are less susceptible to improper expression of repetitive sequences. Most preferably the host will not have a high level of proteases that attack the collagen structure expressed. In this respect *Pichia* or *Hansenula* offers an example of a very suitable expression system. Use of *Pichia pastoris* as an expression system is disclosed in EP-A-0926543 and EP-A-1014176. The microorganism may be free of active post-translational processing mechanism such as in particular hydroxylation of proline and also hydroxylation of lysine. Alternatively the host system may have an endogenic proline hydroxylation activity by which the collagenous polypeptide is hydroxylated in a highly effective way. The selection of a suitable host cell from known industrial enzyme producing fungal host cells specifically yeast cells on the basis of the required parameters described herein rendering the host cell suitable for expression of collagenous polypeptides which are suitable for use as artificial skin in combination with knowledge regarding the host cells and the sequence to be expressed will be possible by a person skilled in the art.

In another embodiment the recombinant collagenous polypeptides have a higher glass transition temperature than natural occurring gelatins. Such sequences are described in WO 05/11740.

The film obtainable using the methods described below has advantageous properties when it is used to make human artificial skin equivalents, using autologous human cells, especially fibroblasts and/or keratinocytes. As shown in the examples, the film enables better (optimized, faster) cell growth compared to cell growth on film comprising high glycosylation and/or low numbers of RGD triplets. This may be due to the enhanced cell-to-film and/or cell-to-cell attachment properties, whereby cell spread across the film is improved. A dense, full thickness artificial skin is obtainable by growing cells on at least one, but preferably both sides of the film. The cells are grown until the skin equivalent is preferably at least about 10, 15, 20 µm thick, or more. Preferably the skin equivalent is "full thickness" (at least about 15-20 µm thick in total). Preferably, multiple layers of cells (e.g. fibroblasts and/or keratinocytes) are grown on at least one, more preferably both sides of the film. This includes the formation of a horny layer.

The method of making an artificial skin comprises the steps of
    producing a film comprising an RGD enriched collagenous polypeptide and/or a polypeptide having a low degree of glycosylation (e.g. no glycosylation);
    contacting the film on one or both sides with live or viable human cells, especially autologous human cells (e.g. fibroblasts and/or keratinocytes);
    incubating the film comprising the cells for a suitable period of time, under suitable conditions for cell growth and optionally repeating the steps of contacting and incubating one or more times.

Cells that can be grown on at least one side of the non-porous film of the invention can be any living, genetically modified or malignant living cell. Preferably normal (healthy) cells, such as those that occur in the human dermis or epidermis, are cultured on the non-porous film. Preferred are human (or mammalian) cells that occur in skin tissue such as fibroblasts, keratinocytes, melanocytes, Langerhans'cells, and the like. In a preferred embodiment the cells are obtained from the subject to be treated (they are "autologous cells"). In one embodiment the invention provides a non-porous film comprising on one side fibroblasts. In another embodiment the invention provides a non-porous film comprising on one side keratinocytes. Preferably the keratinocytes are exposed to air during culturing so that a horny layer (stratum corneum) is formed at the air-culture interface.

In a preferred embodiment a layer comprising fibroblasts on one side of the non-porous film while a layer comprising keratinocytes on the opposite side is provided to avoid that the fibroblasts interfere with keratinocyte growth and differentiation. By exposing the keratinocyte culture to air the formation of horny tissue, hence a stratum corneum, occurs. Thus a full human skin-equivalent is provided comprising a non-porous film according to the present invention comprising on one side thereof a layer comprising fibroblasts and on the opposite side of the layer comprising fibroblasts a layer comprising keratinocytes. In particular the layer comprising keratinocytes comprises at the surface that is not in contact with the non-porous film horny tissue.

After culturing, such a material is suitable for use as artificial skin or as a test substrate for medicines or pharmaceutical or cosmetic compounds, for instance for assessing the permeability of medicines or pharmaceutical or cosmetic compounds through the artificial skin, and/or the influence on cells on either side of the non-porous collagenous polypeptide of the artificial skin or testing properties such of for example UV absorbing compounds. In case of the embodiment having on both sides of the non-porous film cells, in particular fibroblasts and keratinocytes, the non-porous crosslinked gelatin film resembles the basal membrane found in natural skin, thereby providing a full human skin equivalent closely resembling natural skin. This may be of benefit for example in particular for effects of test substrates on skin and also for the treatment of wounds.

Culturing or growing viable or living cells on one or both sides of the film can be done using cell culture methods known in the art and as described in the Examples. Nutrients and other components may either be added together with the cells or separately, and the films comprising the cells are incubated for a sufficient period of time and under suitable conditions for cells growth and/or cells divisions to occur. The non-porous crosslinked gelatin film is particularly suited for the culturing of cells on both sides as the gelatin film has the required physical stability, or mechanical strength, for optimal handling during culturing, in particular in the step of turning the film upside down for culturing the second layer of cells.

The non-porous film may further comprise one or more bioactive compounds such as hormones, growth promoters, antibiotics, immune-suppressors, and the like. Further the non-porous film may comprise one or more compounds that can aid in the wound healing process. A "bioactive compound" is any compound (either a natural compound or a synthetic compound) which exerts a biological effect on other cells. Such compounds are widely available in the art. The compound may be incorporated into the film during its manufacture or, alternatively, it may be added subsequently to one or both sides of the film.

The non-porous film can also be used in cases where skin loss is less extensive but needs to be replaced still, for example in cases of chronic open wounds or in the case of bedsores that occur with for example paralysis.

In another embodiment a method for manufacturing a film according to the invention is provided. This method comprising the steps of:
a) providing a collagenous polypeptide solution of between 2 and 30 weight percent in an aqueous solution,
b) adding a suitable amount of (one or more) crosslinking compound(s) to said aqueous solution, preferably between about 0.02 and 5.0 millimol of (one or more) crosslinking compound(s) per gram collagenous polypeptide (or any other suitable amount as described herein above)
c) coating said collagenous polypeptide solution onto a substrate that was, optionally, first subjected to an adhesion improving treatment of at most 30 watt·minute per square meter
d) drying said coated substrate, and optionally
e) separating the dried non-porous film from the substrate.

Also provided is a method for producing a non-porous film suitable for culturing living or viable cells on at least one side thereof comprising the steps of:
a) providing a collagenous polypeptide solution of between 2 and 30 weight percent in an aqueous solution,
b) coating said collagenous polypeptide solution onto a substrate that was, optionally, first subjected to an adhesion improving treatment of at most 30 watt·minute per square meter
c) drying said coated substrate,
d) subjecting said dried coated substrate to radiation (as described herein above) to form crosslinks between said collagenous polypeptides, and optionally
e) separating the dried non-porous film from the substrate.

The non-porous film of this invention can be produced efficiently and with high speed by coating the collagenous polypeptide solution onto a suitable substrate. The coating solution is prepared by dissolving between about 2 and 30 weight percent of (one or more) collagenous polypeptide(s) in an aqueous solvent. Preferably the concentration of the collagenous polypeptide is between about 5 and 20 weight percent, more preferably between about 10 and 15 weight percent. In case recombinant collagenous polypeptides are used that cannot form stable triple helixes at room temperature or lower temperature, higher concentrations can be used than with natural gelatin or collagen. The aqueous solution contains at least 50 weight percent water, preferably at least 60 weight percent.

An additional solvent may be added to reduce the surface tension of the coating solution in order to improve coatability. Suitable solvents are those that have lower surface tension than water and that in principle can be removed completely by drying. Suitable solvents are for example lower alkyl alcohols such as ethanol, ketones such as acetone, lower alkyl acetates such as ethylacetate and the like. Preferred additional solvents are lower alkyl alcohols such as methanol, ethanol, (iso)propanol. Preferably ethanol is used. Lower alkyl means that the alkyl chain has from 1 to about 6 carbon atoms.

The coating solution is then coated onto a solid substrate. As a coating equipment any method known in the art can be used such as slide bead coating, curtain coating, bar coating, cast coating and the like.

Suitable substrates are substrates having a resin surface such as a polyolefin layer. Preferably the resin layer comprises a polyethylene (PE) or polypropylene (PP), which can be a high density, a low density, a linear low density, a metallocene PE or PP or a mixture thereof. The substrate can also be a paper base coated with a resin layer.

Before coating, the resin surface is optionally subjected to an adhesion promoting treatment such as a flame treatment, a corona treatment or a plasma treatment is necessary of at least 1.5 watt·minute per square meter, preferably at least 2.5 watt·minute per square meter, and at most 30 watt·minute per square meter, preferably at most 25, 20, 15, 10 or 5 watt·minute per square meter. Purpose of the adhesion promoting treatment is to provide enough adhesion so that the material can be coated, dried and subjected to processes such as rolling up or cutting without release of the non-porous film. On the other hand the adhesion should be weak enough to facilitate easy separation from the substrate prior to use for growing or culturing cells.

Just before coating the coating solution onto a substrate, a crosslinking compound(s) may be added. Depending on the desired degree of biodegradability the amount of crosslinking compound(s) added can be between, for example, 0.02 and 0.5 millimol crosslinking compound(s) per gram collagenous polypeptide, between 0.05 and 1 between 0.1 and 2.0, between 0.25 and 2.5, or between 1.0 and 5.0 millimol crosslinking compound(s) per gram collagenous polypeptide.

Adding 'just before coating' or 'immediately prior to coating' means that after addition of crosslinking compound the coating solution is coated onto a substrate before the viscosity increase is too high. The reaction speed of crosslinking and thus the increase of viscosity depends, amongst other factors, on concentrations of both crosslinking compound and collagenous polypeptide. In practical situations the coating liquid is coated within at most about two hours after addition, preferably within at most about 60 minutes, more preferably within at most about 30 minutes after addition of the crosslinking compound to the solution.

Drying can be done by any method known in the art. Preferably the drying conditions, such as humidity and temperature, are controlled so that too fast drying, resulting in cracking or breaking of the film, is prevented.

Before inoculating or contacting the film with one or more cells, the film may optionally be sterilized, for example by exposure to gamma radiation. This can be done before or after peeling (separating) the film from the substrate. Alternatively the whole process is carried out under sterile conditions and by using sterile components, so that the film is sterile prior to being contacted with live or viable cells. The desired cells may also be contacted with one of the surfaces while the film is still attached to the substrate.

In another embodiment the collagenous polypeptides in the film are crosslinked after coating, by exposure to radiation, such as UV-radiation or electron beam. This can replace the addition of crosslinking compound or can be used in combination therewith.

A film obtainable by any of the methods described herein is also an embodiment of the invention.

The film according to the invention may then be contacted with live or viable cells on one and/or both sides of the film. This can be done using known methods, for example inoculating the surface with a cell suspension by pouring or pipetting the (liquid or semi-solid) suspension onto the surface or by or dipping or laying the film surface into/onto the cell suspension. The cells may further be distributed on the film's surface by streaking or other methods. Further, nutrients and or other components may be supplied to the cells and the films are incubated for sufficient time and under suitable conditions to allow cell growth and/or cell division(s).

EXAMPLES

Preparation of a Non-Porous Film or Film of this Invention

A natural gelatin or a recombinantly produced collagenous polypeptide, as described for example in EP-A-1398324, of a molecular weight up to 100 kilo Dalton is dissolved in demineralized water at a temperature of 40° C. After the polypeptide is dissolved the temperature is increased to 60 degrees Celsius for 30 minutes to fully uncurl the gelatin or collagen strands, after which the temperature is decreased again to 40 degrees Celsius. To improve wetability 15~30% (weight/weight) 96% pure EtOH is added to obtain final collagenous polypeptide concentrations of 10~25% (weight/weight).

Depending on the cross-linking compound the pH is adjusted with 1M NaOH or 1M HCl to 5~6 when using glutaraldehyde (GTA: 25% solution (weight/weight)) and to 7~8 when using N-Ethyl-N'-(3-Dimethyl aminopropyl)carbodiimide.HCl (EDC: 25% solution (weight/weight)).

The crosslinking compound is added to the gelatin solution just before coating, that is, before viscosity due to crosslinking becomes too high.

The collagenous polypeptide solution is thoroughly mixed with the crosslinking compound solution and directly after mixing coated on a polyethylene substrate. Wet coating thickness of 100~400 μm is applied which after drying results in dry membrane thickness of 10~100 μm.

Drying may be done for example at ambient conditions for at least 24 h.

After drying, films are cut and irradiated with gamma rays at a doses of at least 25 kGy to realize sterile gelatin films Culture of Keratinocytes and Fibroblasts:

Keratinocytes and fibroblasts were isolated from normal human skin obtained from breast surgery. Keratinocytes were grown in keratinocyte medium using 3 parts of Dulbecco's modified eagles medium (DMEM) and 1 part of Ham's F12 medium supplemented with 5% serum (fetal calf) and various other additives e.g 100 microgram streptomycin/ml and 100 I.U. penicillin/ml. For establishment of human skin equivalents keratinocytes of passage 2 were used. Fibroblasts were grown in DMEM, supplemented with 5% calf serum. For fabrication of skin equivalents fibroblasts of passage 2-9 were used. Keratinocytes and fibroblasts were grown to confluence in plastic tissue culture dishes.

Preparation Method of Human Skin Equivalents:

The collagenous polypeptide films were washed during 24 hours in buffered saline solution at room temperature. After 1 and 2 hours, the buffered saline solution was refreshed. After washing, fibroblasts were seeded onto the films and either a. incubated for 3 days in fibroblast medium with 5% serum, 1 nanogram/ml Epidermal Growth Factor (EGF) and various other additives.

b. incubated for 3 days in fibroblast medium with 1% serum, 1 nanogram/ml EGF and various other additives. During this culture period—at day two—keratinocytes were seeded onto the backside of the collagenous polypeptide films.

Human skin equivalents are grown onto metal grid supports.

After 3 days, the combined keratinocyte/fibroblast cultures were lifted to the air-liquid interface and cultured in DMEM/

Ham's F12 medium supplemented with 1 nanogram/ml EGF, in the absence of serum. Cells were grown for an additional 10 days to confluence.

Example 1

Preparation of Nonporous Film from a Recombinantly Produced Tetramer of 72.6 Kilo Dalton as Described in EP-A-1398324

Totally 11.4 g of the tetramer was dissolved in 34.2 g demineralized water at 40 degrees Celsius. After dissolving, the temperature was increased to 60 degrees Celsius for 30 minutes and then decreased again to 40 degrees Celsius. Additional 11.4 g EtOH (96% pure) was added. pH of the solution was adjusted with 1M NaOH to 7.5.

25% EDC (N-Ethyl-N'-(3-Dimethyl aminopropyl)carbodiimide.HCl) solution was prepared by dissolving 1 g EDC in 3 g demineralized water.

Additions of the crosslinking compound solution to the collagenous polypeptide solutions were done according table 1. After addition the mixtures were stirred thoroughly and the mixtures were applied on non-treated photographic base-paper with a polyethylene top layer. With a spirally wound 'Large K Hand Coater Bar' No. 125 a wet film deposit of 125 1.1M was coated on A4 sized substrates. The coated films were left to dry at room temperature for at least 24 h.

Dry thickness was measured using a Lorentzen & Wettre micrometer type 221. Swelling can be measured with a method as described by Flynn and Levine (Photogr. Sci. Eng., 8, 275 (1964).

Physical strength was determined qualitatively by manually handling a film. The designation '−' means too weak, '+' no tear during normal handling, '+/−' means that in about 50 percent of the tests the film tore and '++' means no tear even after applying more force than necessary. Brittleness was also tested qualitatively in a similar manner by bending the film. Results of dry thickness, water swelling (vertical) and physical properties are also listed in table 1:

TABLE 1

| Solution | EDC/Lysine ratio (mol/mol) | Dry thickness (micron) | Swelling (micron) | Physical strength | brittleness |
|---|---|---|---|---|---|
| I | 0.4 | 25 | 159 | +/− | + |
| II | 0.5 | 24 | 138 | + | + |
| III | 0.6 | 22 | 133 | +/++ | + |
| IV | 1.0 | 23 | 64 | ++ | + |
| V | 2.0 | 21 | 54 | − | − |

Figure 1:
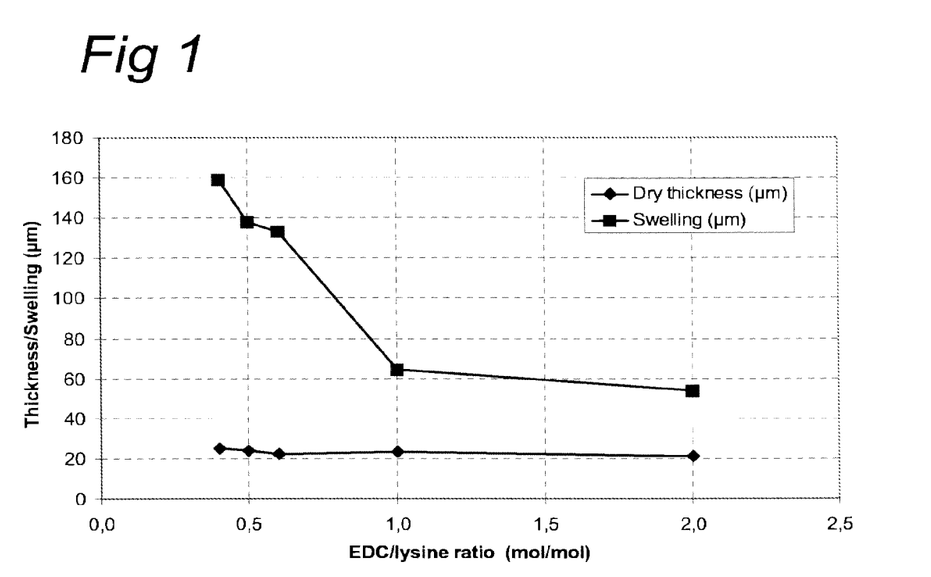
FIG. 1: Effect of crosslinking on initial thickness and swelling of a non-porous film. The graph shows the EDC/lysine ratio (tetramer example 1, 72.6 kDa) vs dry thickness (μm) and swelling (μm, $H_2O$ 37° C.).

See FIG. 1 for the graphic processing of the swelling data.

The obtained films were cut to circular membranes with a diameter of 27 millimeter and were sterilized by means of gamma irradiation with a doses of at least 25 kGy.

Preparation Method of Full Human Skin Equivalent:
A gelatin membrane was placed in a petridish (using a pair of tweezers);
Phosphate buffered saline solution was added to the petridish for washing the membrane (at RT). After 2 hrs. the PBS solution was removed by a pipette and fresh PBS solution was added to the membrane;
After 1 day PBS solution was removed (by pipette) and fibroblast culture medium was added for an additional washing step;
After 2 hrs culture medium solution was removed by pipette and fibroblasts were seed on the membrane;
The cells were allowed to attach to the membrane for ~1 h;
The fibroblast culturing medium was added in such an amount that the membrane was not air-exposed since fibroblasts have to grow under wet conditions;
Culturing took place for 1 week, 2 times per week culture medium was refreshed (removal by pipette);
Membrane with fibroblasts was turned upside down using a Millipore filter (TETP02500, 8 μm). The membrane was lifted via a pair of tweezers and put upside down on a metal grid;
The medium was changed to keratinocyte medium as described above;
Keratinocytes were seeded on the backside of the gelatin membrane in a metal ring (to prevent dispersion of the cells). After adherence of the keratinocytes the metal ring was removed and the culture continued for another 7 days;
After 7 days, the cultures were exposed to the air interface and cultured for another 14 days; culture medium was refreshed 2 times per week); no extra handlings were needed since the amount of medium was reduced so that the keratinocytes remained above the liquid surface.

Evaluation of Full Human Skin Equivalent:
skin equivalents were harvested and fixed in 4% paraformaldehyde, dehydrated and embedded in paraffine; then the embedded tissue was cut into slices and stained with haematoxyline/eosine;
Stained slices were visualized by light microscope;
Clearly several layers (multilayer) of keratinovcytes were visible having on the air-exposed side thereof horny tissue (stratum corneum); fibroblasts were separated from the keratinocytes by the gelatin membrane.

Example 2

In Vitro Degradation of the Cross-Linked Membranes

Bacterial collagenase (activity of >125 CDU/mg (One Collagen Digestion Unit liberates peptides from collagen equivalent in ninhydrin color to 1.0 μmole of leucine in 5 hr at pH 7.4 at 37° C. in the presence of calcium ions)) from *Clostridium histolyticum* (Sigma-Aldrich, EC 3.4.24.3) was selected as an enzyme for the degradation studies because of its specificity for collagen. These collagenase preparations contain at least six different collagenases which are capable of cleaving peptide bonds within the triple helical structure and have a specificity for the Pro-X-Gly-Pro-Y region, splitting between X and Gly.

In a typical degradation experiment, a 10 milligram sample of cross-linked collagenous polypeptide with either GTA or EDC is immersed in 0.5 ml of a 0.1 M Tris-HCl buffer solution (pH 7.4) containing 0.005M $CaCl_2$ and 0.05 mg/ml sodium azide and incubated at 37° C. After one hour, 0.5 ml collagenase solution in Tris-HCl buffer (37° C.) was added to give the desired final concentration and absolute amount of collagenase (100 CDU/ml or 10 CDU/mg collagenous polypeptide).

The degradation was discontinued at the desired time interval by the addition of 0.1 ml 0.25M EDTA (Titriplex III) and cooling of the system.

The weight-loss of the cross-linked collagenous polypeptide samples during the degradation was determined by a gravimetrical method.

Samples were dried overnight under vacuum over KOH and were weighted. Thereafter the samples were degraded as described above. After a pre-determined degradation period, EDTA was added and the tubes were centrifuged at 600 G for 10 minutes and the remaining solution was discarded. The resulting pellet was washed with distilled water and centrifuged. This washing procedure was conducted three times in total. After the final washing step, the remaining pellet was freeze dried and weighted to determine the weight-loss of the collagenous polypeptide samples.

Figure 2:
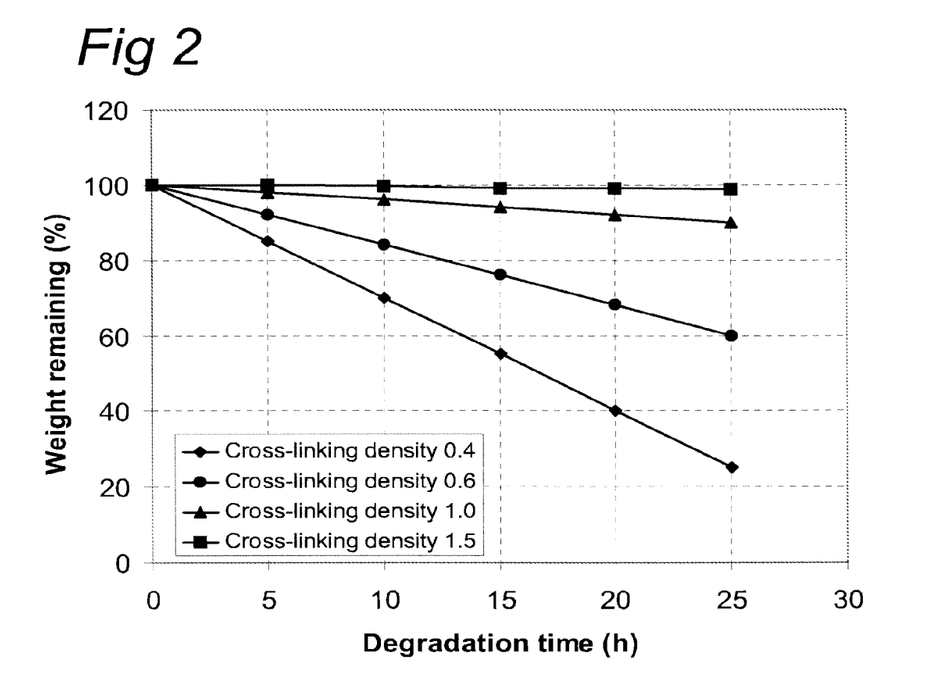
FIG. 2: Effect of crosslinking on degradation speed of a non-porous film. The graph shows the degradation speed of EDC cross-linked tetramer (72.6 kDa) to a bacterial collagenase solution with 10 CDU/mg gelatin.

See FIG. 2 for the graphical presentation of the data.

Example 3

Permeability and Degradation Level Vs. Cross-Link Density

To determine the permeability of the prepared membranes a diffusion experiment was initiated. 193 mg of Lysozyme, a globular protein of 14.3 kDa, was dissolved in 5 ml physiological salt solution to obtain a lysozyme concentration of 38.6 mg/ml (donor solution).

Figure 3:
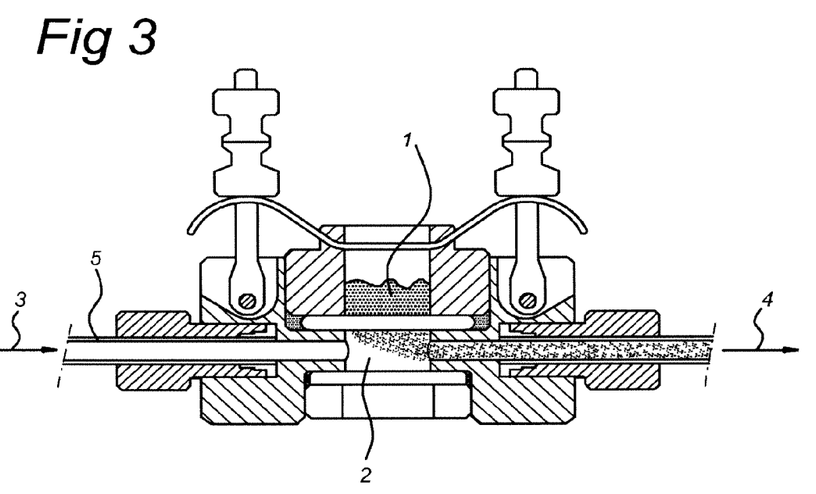
FIG. 3: Diffusion cell for testing permeability of a non-porous film, wherein 1=donor compound, 2=receptor compartment, 3=receptor input, 4=compound and receptor output for analysis, 5=⅛" OD×1/32" wall tubing.

The EDC cross-linked gelatin membranes with a cross-linking density of 0.4, 0.6, 1.0 and 1.5 EDC/lysine (mol/mol) were mounted in the diffusion cells (see FIG. 3) and 300 µl of the donor solution was put on top of the mounted membranes.

The receptor fluid (also physiological salt solution) flow is 1 ml/hr. During the whole experiment the temperature of the system was kept at 37° C.

The first fraction of 5 ml and the diluted donor solution were analyzed by means of GPC at a wavelength of 280 nm.

Figure 4:
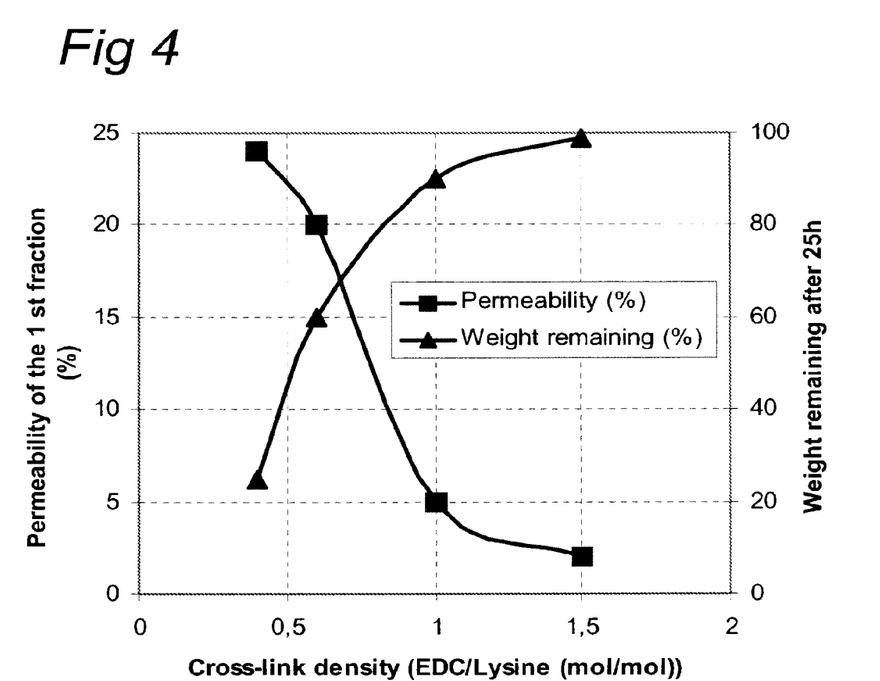
FIG. 4: Effect of crosslinking on permeability and degradation of a non-porous film. The graph shows the permeability for lysozyme (14.3 kDa, 1st fraction) and degradation (weight remaining) after 25 h of EDC cross-linked tetramer (72.6 kDa) to a collagenase solution with 10 CDU/mg gelatin.

The results were compared to the degradation level (weight remaining %) after 25 h. See FIG. 4 for the graphical presentation of the data which show that both parameters, permeability and degradation, can be controlled by the cross-linking density.

Example 4

Effect of RGD Triplets and/or Glycosylation of the Collagenous Polypeptide on Cell Growth Method:

To test glycosylation and/or RGD triplet numbers on human cell growth, various polypeptides were made.

Results:

| Glycosylation (m/m)% | Nr. of RGD triplets | Cell growth |
| --- | --- | --- |
| 7-9 | 0 | Very bad |
| 1-2 | 0 | bad |
| 1-2 | 1 | moderate |
| ≦1-2 | 5 | Very good |

The invention claimed is:

1. A non-porous film having an average pore size of less than 1 µm as determined by scanning electron microscope, comprising a collagen polypeptide comprising at least one GXY domain having a length of at least 5 consecutive GXY triplets, wherein X and Y each represent any amino acid and wherein at least 20% of the amino acids of said collagen polypeptide are present in the form of consecutive GXY triplets, wherein the film has a thickness, when placed in demineralized water of 37° C. for 24 hours, is at most 10 times its initial thickness, wherein the film is crosslinked by:
  (i) adding between 0.02 millimol and 5.0 millimol of a crosslinking compound per gram collagenous polypeptide, or
  (ii) exposing the film to radiation so that the degree of crosslinking is the equivalent of adding between 0.02 millimol and 5.0 millimol of a crosslinking compound per gram collagenous polypeptide.

2. The non-porous film according to claim 1, wherein said collagen polypeptide is selected from the group consisting of gelatin, natural collagen, modified collagen, synthetic collagen, and recombinant collagen.

3. The non-porous film according to claim 1, wherein the collagen polypeptide has at least 0.4 percent RGD motifs.

4. The non-porous film according to claim 1, wherein the collagen polypeptide has a content of glycosylation of less than or equal to 2 (m/m) %.

5. The non-porous film according to claim 1, wherein the degree of crosslinking is the equivalent of adding between 0.5 millimol and 2.0 millimol of a crosslinking compound per gram collagen polypeptide.

6. The non-porous film according to claim 1, wherein said crosslinking compound is selected from the group consisting of glutaraldehyde, water-soluble carbodiimides, bisepoxy compounds, formalin and 1-ethyl-3-(3-dimethylaminopropyl)carbodiimide.

7. The non-porous film according to claim 1, wherein said film further comprises one or more bioactive compounds.

8. The non-porous film according to claim 7, wherein said one or more bioactive compounds are selected from the group consisting of a hormone, a growth promoter, an antibiotic and an immune-suppressor.

9. The non-porous film according to claim 1, wherein said film comprises on one side a layer comprising fibroblasts and on the opposite side a layer comprising keratinocytes.

10. The non-porous film according to claim 9, wherein the layer comprising keratinocytes comprises, at the surface that is not in contact with the non-porous film, horny tissue.

11. The non-porous film according to claim 2, wherein said crosslinking compound is selected from the group consisting of glutaraldehyde, water-soluble carbodiimides, bisepoxy compounds, formalin and 1-ethyl-3-(3-dimethylaminopropyl)carbodiimide.

12. A method of producing a material for treating wounds or as a test substrate comprising the steps of:
  (a) obtaining a non-porous film according to claim 1, and
  (b) culturing a layer of fibroblasts on one side of said film, and/or
  (c) culturing a layer of keratinocytes on the opposite side of said film.

13. A method of treating skin wounds comprising administering to the wound a non-porous film according to claim 1.

* * * * *